(12) United States Patent
SaNogueira et al.

(10) Patent No.: US 6,830,746 B2
(45) Date of Patent: Dec. 14, 2004

(54) SUNSCREEN COMPOSITIONS

(75) Inventors: James SaNogueira, Suffern, NY (US); Jennifer Fuller, Mahwah, NJ (US)

(73) Assignee: Playtex Products, Inc., Westport, CT (US)

( * ) Notice: Subject to any disclaimer, the term of this patent is extended or adjusted under 35 U.S.C. 154(b) by 132 days.

(21) Appl. No.: 09/957,920

(22) Filed: Sep. 21, 2001

(65) Prior Publication Data

US 2003/0059383 A1 Mar. 27, 2003

(51) Int. Cl.$^7$ .......................... A61K 7/42; A61K 7/44; A61K 7/00; C07G 3/00
(52) U.S. Cl. .......................... 424/59; 424/60; 424/400; 424/401; 514/937; 514/938; 514/939; 514/943; 536/1.1; 536/4.1
(58) Field of Search .......................... 424/59, 60, 400, 424/401; 536/1.1, 4.1; 514/937, 938, 939, 943

(56) References Cited

U.S. PATENT DOCUMENTS

| | | | |
|---|---|---|---|
| 4,656,029 A | 4/1987 | Grollier et al. | 414/47 |
| 5,032,390 A | 7/1991 | Iwaya et al. | 424/59 |
| 5,093,107 A | 3/1992 | Matravers | 424/59 |
| 5,208,011 A | 5/1993 | Vaughan | 424/59 |
| 5,208,013 A | 5/1993 | Klein | 424/59 |
| 5,306,486 A | 4/1994 | McCook et al. | 424/59 |
| 5,372,805 A | 12/1994 | Finkel et al. | 424/59 |
| 5,417,961 A | 5/1995 | Nearn et al. | 424/59 |
| 5,486,631 A | 1/1996 | Mitchnick et al. | 556/10 |
| 5,543,136 A | 8/1996 | Aldous | 424/59 |
| 5,554,374 A | 9/1996 | Olivier-Terras | 424/401 |
| 5,571,503 A | 11/1996 | Mausner | 424/59 |
| 5,614,178 A | 3/1997 | Bloom et al. | 424/60 |
| 5,658,580 A | 8/1997 | Mausner | 424/401 |
| 5,667,765 A | 9/1997 | Hansenne et al. | 424/59 |
| 5,672,337 A | 9/1997 | Ascione et al. | 424/59 |
| 5,676,934 A | 10/1997 | Siegfried | 424/59 |
| 5,725,844 A | 3/1998 | Gers-Barlag et al. | 424/59 |
| 5,730,993 A | 3/1998 | Allard et al. | 424/401 |
| 5,733,531 A | 3/1998 | Mitchnick et al. | 424/59 |
| 5,770,183 A | 6/1998 | Linares | 424/59 |
| 5,776,438 A | 7/1998 | Tokue et al. | 424/59 |
| 5,788,954 A | 8/1998 | Bonda et al. | 424/59 |
| 5,804,168 A | 9/1998 | Murad | 424/59 |
| 5,827,508 A | 10/1998 | Tanner et al. | 424/59 |
| 5,843,411 A | 12/1998 | Hernandez et al. | 424/59 |
| 5,851,544 A | 12/1998 | Penska et al. | 424/401 |
| 5,891,452 A | 4/1999 | Sebillote-Arnaud et al. | 424/401 |
| 5,902,591 A | 5/1999 | Herstein | 424/401 |
| 5,916,542 A | 6/1999 | Fossati | 424/59 |
| 5,916,544 A | 6/1999 | Liu et al. | 424/59 |
| 5,922,331 A | 7/1999 | Mausner | 424/59 |
| 5,948,416 A | 9/1999 | Wagner et al. | 424/401 |
| 5,951,990 A | 9/1999 | Ptchelintsev | 424/401 |
| 5,961,961 A | 10/1999 | Dobkowski et al. | 424/59 |
| 5,968,529 A | 10/1999 | Horino et al. | 424/401 |
| 5,976,513 A | 11/1999 | Robinson | 424/59 |
| 5,976,555 A * | 11/1999 | Liu et al. | 424/401 |
| 6,015,548 A | 1/2000 | Siddiqui et al. | 424/59 |
| 6,024,941 A | 2/2000 | Yanagida et al. | 424/59 |
| 6,036,945 A | 3/2000 | Deblasi et al. | 424/59 |
| 6,039,935 A | 3/2000 | Mohammadi | 424/59 |
| 6,043,204 A | 3/2000 | Kaufman et al. | 510/130 |
| 6,048,517 A | 4/2000 | Kaplan | 424/60 |
| 6,066,327 A | 5/2000 | Gubernick et al. | 424/401 |
| 6,068,848 A | 5/2000 | Gubernick et al. | 424/401 |
| 6,071,501 A | 6/2000 | Robinson | 424/59 |
| 6,090,369 A | 7/2000 | Stewart | 424/59 |
| 6,110,477 A | 8/2000 | Hernandez et al. | 424/401 |
| 6,123,928 A | 9/2000 | Sovak et al. | 424/59 |
| 6,130,254 A | 10/2000 | Fisher et al. | 514/725 |
| 6,132,737 A | 10/2000 | Wolf et al. | 424/401 |
| 6,153,205 A | 11/2000 | Boussouira et al. | 424/401 |
| 6,153,208 A | 11/2000 | McAtee et al. | 424/402 |
| 6,162,450 A | 12/2000 | Ptchelintsev et al. | 424/401 |
| 6,171,580 B1 | 1/2001 | Katsuyama et al. | 424/59 |
| 6,171,602 B1 | 1/2001 | Roman | 424/401 |

\* cited by examiner

Primary Examiner—Shelley A. Dodson
(74) Attorney, Agent, or Firm—Ohlandt, Greeley, Ruggiero, Perle, LLP

(57) ABSTRACT

The present invention is a sunscreen composition that has at least one sunscreen agent and at least one glucoside emulsifier. The composition also has water. Preferably, the sunscreen composition also has at least one of the following additional components: emulsifier other than glucoside, emollient, skin-feel additive, moisturizing agent, film former/waterproofing agent, pH adjuster/chelating agent, preservative, or any combinations thereof. The composition is a stable oil-in-water emulsion.

41 Claims, No Drawings

SUNSCREEN COMPOSITIONS

BACKGROUND OF THE INVENTION

I. Field of the Invention

The present invention relates to sunscreen compositions. More particularly, the present invention relates to sunscreen compositions that have enhanced sensory properties when applied.

II. Description of the Prior Art

Sunscreen compositions are applied to the skin to protect the skin from the sun's ultraviolet rays that can lead to erythema, a reddening of the skin also known as sunburn. Sunlight or ultraviolet radiation in the UV-B range has a wavelength of 290 nm to 320 nm and is known to be the primary cause of sunburn. Ultraviolet rays at a wavelength of 320 nm to 400 nm, known as UV-A radiation, produces tanning of the skin. However, in the process of doing so, the UV-A rays can damage or harm the skin.

Besides the immediate malady of sunburn, excessive sunlight exposure can lead to skin disorders. For instance, prolonged and constant exposure to the sun may lead to actinic keratoses and carcinomas. Another long-term effect is premature aging of the skin. This condition is characterized by skin that is wrinkled, cracked and has lost its elasticity.

As stated above, sunscreens are typically formulated with the goal of inhibiting skin damage from the sun's rays. The sunscreen composition filters or blocks the harmful UV-A and UV-B rays that can damage and harm the skin. It is believed that sunscreen agents accomplish this by absorbing the UV-A and/or UV-B rays.

In general, sunscreen compositions are oil-in-water emulsions. In this system, the UV-absorbing compounds are typically incorporated into the oil phase.

Consumers consider many factors when purchasing a sunscreen product, such as, the sun protection factor (SPF), how durable the product is after applying it over the skin, the shelf life of the product, and product form (i.e., lotions, gels, creams, and sprays). Another important and influential property of a sunscreen product considered by a consumer is how the product feels and how well it spreads over the skin. Typically, consumers want a sunscreen that feels soft and silky and can be applied in a smooth, continuous film over the skin. Ultimately, product feel could determine whether the consumer decides to purchase the product.

The sunscreen compositions of the present invention provide the user with an enhanced soft, silky feel when applied to skin while still providing superior protection from damaging ultraviolet light.

SUMMARY OF THE INVENTION

It is an object of the present invention to provide a sunscreen composition that can be effectively applied as a lotion.

It is another object of the present invention to provide such a sunscreen composition that has an enhanced soft, silky feel when applied to the skin.

It is still another object of the present invention to provide such a sunscreen composition that spreads uniformly over the skin.

It is yet another object of the present invention to provide such a sunscreen composition that is a stable oil-in-water emulsion.

To accomplish the foregoing objects and advantages, the present invention, in brief summary, is a sunscreen composition that has at least one sunscreen agent, at least one glucoside emulsifier, and water. Preferably, the sunscreen composition also contains at least one of the following additional components: an emulsifier other than glucoside, emollient, skin-feel additive, moisturizing agent, film former/waterproofing agent, pH adjuster/chelating agent, preservative, or any combinations thereof.

DETAILED DESCRIPTION OF THE INVENTION

The present invention is a sunscreen composition that is provided as a stable oil-in-water emulsion. The composition includes at least one sunscreen agent and at least one glucoside emulsifier. The composition also has water. Preferably, the sunscreen composition also has one or more of the following additional components: an emulsifier other than glucoside, emollient, skin-feel additive, moisturizing agent, film former/waterproofing agent, pH adjuster/chelating agent, preservative, or any combinations thereof.

The sunscreen composition of the present invention is uniquely formulated to provide an enhanced feeling of softness and silkiness when the sunscreen composition is applied to the skin. Moreover, the composition is capable of being easily and uniformly applied over the skin. These enhanced properties are achieved, in large part, by formulating the sunscreen composition as a stable oil-in-water emulsion, where the oil phase has an amount of glucoside emulsifier such that the unexpected soft, silky properties are realized when the sunscreen is applied to the skin.

The one or more sunscreen agents that can be used in the present invention must be capable of absorbing or blocking the harmful effects of ultraviolet radiation. In addition, they must be non-toxic and non-irritating when applied to the skin. Suitable sunscreen agents that may be used in the sunscreen composition include, for example, para-aminobenzoic acid (PABA), butyl methoxydibenzoylmethane (avobenzone), benzophenone-1, benzophenone-2, benzophenone-3, benzophenone-4, benzophenone-6, benzophenone-8, benzophenone-12, methoxycinnamate, ethyl dihydroxypropyl-PABA, glyceryl PABA, homosalate, methyl anthranilate, octocrylene, octyl dimethyl PABA, octyl methoxycinnamate, octyl salicylate, PABA, 2-phenylbenzimidazole-5-sulphonic acid, triethanolamine salicylate, 3-(4-methylbenzylidene)-camphor, red petrolatum, zinc oxide, titanium dioxide, 3-(4-methylbenzyldine)boran-2-one(methylbenzindinecamphor), benzotriazole, phenylbenzimidazole-5-sulfonic acid, methylene bis-benzotrizolyl tetramethylbutyl phenol, or any mixtures thereof.

The preferred sunscreen agents are avobenzone, benzophenone-3, octyl methoxycinnamate, octyl salicylate, homosalate, zinc oxide, or any mixtures thereof.

The one or more sunscreen agents are included in a present composition at about 1 weight percent (wt. %) to about 40 wt. % of the total weight of the composition. The amount of sunscreen agent in the composition will vary in the above range depending on the sun protection factor (SPF) desired. The higher the SPF, the greater the total amount of sunscreen agent. Preferably, the one or more sunscreen agents are included at about 4 wt. % to about 35 wt. % to achieve a SPF of about 2 to about 50.

As noted above, it has been discovered that the inclusion of one or more glucoside emulsifiers in the sunscreen compositions of the present invention results in compositions that have an enhanced soft, silky feel when applied to the skin. Preferably, the one or more glucoside emulsifiers are selected from the group consisting of: cetearyl glucoside, cocoyl glucoside, cocoyl ethyl glucoside, disodium coco-glucoside citrate, disodium coco-glucoside sulfosuccinate, lauroyl ethyl glucoside, myristoyl ethyl glucoside, octyl dimethicone ethoxy glucoside, oleoyl ethyl glucoside, sodium coco-glucoside tartrate, or any mixtures thereof. Most preferably, the glucoside emulsifier is cocoyl glucoside mixed with cetearyl alcohol. This mixture is sold under the tradename MONTONOV® 82 by SEPPIC. It has been unexpectedly found that the inclusion of MONTONOV® 82 imparts an exceptional and enhanced soft, silky feel to a user's skin when a sunscreen composition of the present invention is applied.

The amount of glucoside emulsifier present in a sunscreen composition of the present invention is about 1 wt. % to about 10 wt. % of the total weight of the composition. Preferably, the glucoside emulsifier is present in an amount about 2.5 wt. % to about 7.5 wt. % of the total weight of the composition.

The compositions of the present invention also include water. Water is present in an amount about 45 wt. % to about 75 wt. %, and preferably about 50 wt. % to about 65 wt. %, of the total weight of the sunscreen composition.

In addition to the one or more glucoside emulsifiers, one or more additional emulsifiers may also be included in the sunscreen compositions of the present invention. The one or more additional emulsifiers, in conjunction with the one or more glucoside emulsifiers, enable two or more immiscible liquids to be combined homogeneously, while increasing the viscosity of the composition. Moreover, the emulsifiers act to stabilize the composition.

One or more additional emulsifiers that can be used in the present invention include, for example, butylated PVP, cetyl alcohol, sodium acrylate/sodium acryloyldimethyltaurate copolymer, diethylhexyl napthalate, sorbitan oleate, sorbitan sesquioleate, sorbitan isostearate, sorbitan trioleate, polyglyceryl-3-diisostearate, polyglycerol esters of oleic/isostearic acid, polyglyceryl-6 hexaricinolate, polyglyceryl-4-oleate, polygylceryl-4 oleate/PEG-8 propylene glycol cocoate, oleamide DEA, sodium glyceryl oleate phosphate, hydrogenated vegetable glycerides phosphate, or any mixtures thereof.

The preferred additional emulsifiers are butylated PVP, cetyl alcohol, sodium acrylate/sodium acryloyldimethyltaurate copolymer, diethylhexyl napthalate, or any mixtures thereof.

The amount of additional emulsifier present in a sunscreen composition of the present invention is about 0.01 wt. % to about 5 wt. % of the total weight of the composition. Preferably, one or more emulsifiers in an amount about 0.05 wt. % to about 2 wt. % of the total weight of the composition are used.

The present composition may include one or more emollients. An emollient provides a softening or soothing effect on the skin surface and is generally considered safe for topical use. It also helps control the rate of evaporation and the tackiness of the sunscreen composition.

Suitable emollients include, for example, cyclomethicone, dimethicone, dicapryl maleate, caprylic/capric triglyceride, mineral oil, lanolin oil, coconut oil, cocoa butter, olive oil, aloe extracts such as aloe vera, jojoba oil, castor oil, fatty acid such as oleic and stearic, fatty alcohol such as cetyl and hexadecyl (ENJAY), diisopropyl adipate, hydroxybenzoate esters, benzoic acid esters of $C_9$–$C_{15}$ alcohols, isononyl iso-nonanoate, alkanes such as mineral oil, silicone such as dimethyl polysiloxane, ether such as polyoxypropylene butyl ether and polyoxypropylene cetyl ether, $C_{12}$–$C_{15}$ alkyl benzoate, or any mixtures thereof.

The preferred emollients are cyclomethicone, dimethicone, dicapryl maleate, caprylic/capric triglyceride, aloe vera, or any mixtures thereof.

The total amount of emollient present in the sunscreen composition is typically about 0.10 wt. % to about 30 wt. % of the total weight of the composition. The preferred amount of emollient is about 1 wt. % to about 20 wt. %.

As stated above, the feel of the sunscreen composition upon application to the skin may be the ultimate consideration of a consumer when purchasing a sunscreen. Moreover, a smooth, silky sunscreen composition may be more uniformly applied over the skin. To further enhance the feel of the sunscreen compositions of the present invention when applied to the skin, a skin-feel additive may be included. Suitable skin-feel additives include, for example, synthetic polymers, silicones, esters, particulates, or any mixtures thereof. Preferably, the skin-feel additive is a synthetic polymer, nylon-12. Nylon-12 includes microscopic nylon beads, which act like ball bearings on the skin. Therefore, when the composition is applied to the skin, an enhanced silky, smooth feeling results and the composition can be applied evenly over the skin. Also, the nylon-12 has unexpectedly been found to absorb the oil in the sunscreens upon application. Thus, the nylon-12 adds slip to the composition without imparting an undesirable greasy feel.

Preferably, the skin-feel additive is present in a present sunscreen composition in an amount about 0.10 wt. % to about 5 wt. % of the total weight of the composition. More preferably, it is present in an amount about 0.30 wt. % to about 0.70 wt. % of the total weight of the composition.

The pH of the compositions of the present invention may be adjusted by one or more basic pH adjusters and/or chelating agents. For example, sodium hydroxide, triethanolamine, trisodium ethylenediaminetetraacetic acid, or any mixtures thereof are suitable pH adjusters/chelating agents that may be included in the sunscreen compositions of the present invention.

An effective amount of a pH adjuster and/or chelating agent that may be included to adjust the pH of the final composition to about 3 to about 9. Preferably, the pH is adjusted to about 6 to about 8.

A moisturizing agent, such as a humectant, may be used in the compositions of the present invention. Suitable humectants include, but are not limited to, glycerin, polyethylene glycol, polypropylene glycol, sorbitol, PEG-4, or any mixtures thereof.

One or more moisturizing agents are optionally included in the compositions of the present invention in an amount about 0.1 wt. % to about 1 wt. % of the total weight of the composition. Preferably, about 0.25 wt. % to about 0.75 wt. % of one or more moisturizing agents may be used in the composition.

Another component that may be used in a sunscreen composition of the present invention is a film former/waterproofing agent. The film former/waterproofing agent is a hydrophobic material that imparts film forming and waterproofing characteristics to the emulsion. One such agent is polyethylene, which is available from New Phase Technologies as PERFORMALENE® 400, a polyethylene having a molecular weight of 400. Another suitable water-proofing agent is polyethylene 2000 (molecular weight of 2000), which is available from New Phase Technologies as PERFORMALENE® 2000. Yet, another suitable film former/waterproofing agent is synthetic wax, also available from New Phase Technologies as PERFORMA® V-825. One or more film formers/waterproofing agents may be present in a composition of the present invention in an amount about 0.1 wt. % to about 5 wt. % of the total weight of the composition.

Optionally, one or more preservatives may be included in a composition of the present invention. The preservative protects the composition from microbial contamination and/or oxidation. As such, the preservative can include an antioxidant. Preservatives, such as diazolidinyl urea, iodopropynyl butylcarbamate, chloromethylisotiazolinone, methylisothiazolinone, vitamin E and its derivatives including vitamin E acetate, vitamin C, butylated hydroxytoluene, methylparaben, or any mixtures thereof, may be included as a preservative in a composition of the present invention.

About 0.01 wt. % to about 1 wt. % of preservative may be included in a composition of the present invention. Preferably, one or more preservatives total about 0.05 wt. % to about 0.50 wt. % of the total weight of the composition.

The sunscreen compositions of the present invention may also have other optional additives. For instance, one or more fragrances, colorants, plant extracts, absorbents, thickeners, salicylic acid, alpha and beta hydroxy acids, vitamins including vitamins A, C, and E, retinol, retinol palmitate, vitamin E acetate, tocopherol, vitamin A palmitate, vitamin E palmitate, or any mixtures thereof, may be included in the sunscreen compositions.

The components of the present invention may be combined to form a stable oil-in-water emulsion. The sunscreen is incorporated into the oil phase and later combined with water with the help of the one or more emulsifiers. The process used to manufacture the composition of the present invention must be capable of forming a homogeneous composition that can be spread into a film.

In one preferred embodiment of the present invention, the sunscreen composition includes about 6 wt. % to about 12 wt. % of one or more sunscreen agents selected from the group consisting of: octyl methoxycinnamate, octyl salicylate, butyl methoxydibenzoylmethane, or any mixtures thereof; and about 4 wt. % to about 6 wt. % of MONTONOV® 82. This composition has been found to have an enhanced soft, silky feel when applied to the skin. In addition, this composition has a SPF of at least 15. In a more preferred embodiment, this composition also includes about 0.25 wt. % to about 1 wt. % of nylon-12, which further enhances the soft, silky feel of the composition when applied to the skin.

In a second preferred embodiment of the present invention, the sunscreen composition includes about 15 wt. % to about 25 wt. % of one or more sunscreen agents selected from the group consisting of: octyl methoxycinnamate, octyl salicylate, benzophenone-3, butyl methoxydibenzoylmethane, or any mixtures thereof; and about 4 wt. % to about 6 wt. % of MONTONOV® 82. This composition also has been found to have an enhanced soft, silky feel when applied to the skin. In addition, this composition has a SPF of at least 30. In a more preferred embodiment, this composition also includes about 0.25 wt. % to about 1 wt. % of nylon-12, which further enhances the soft, silky feel of the composition when applied to the skin.

In a third preferred embodiment of the present invention, the sunscreen composition includes about 20 wt. % to about 30 wt. % of one or more sunscreen agents selected from the group consisting of: octyl methoxycinnamate, octyl salicylate, benzophenone-3, zinc oxide mixed with alkyl banzoate, or any mixtures thereof; and about 4 wt. % to about 6 wt. % of MONTONOV® 82. This composition has been found to also have an enhanced soft, silky feel when applied to the skin. In addition, this composition has a SPF of at least 50.

The sunscreen compositions may be prepared by using techniques and methods well known in the art. In general, ingredients are incorporated by mixing and applying heat if necessary, until the composition is uniform and homogeneous. The composition may be homogenized to ensure homogeneity and to build the proper viscosity. The sunscreen compositions of the present invention are then packaged as a lotion in any package or container suitable for a sunscreen composition.

Having thus described the present invention with particular reference to preferred embodiments thereof, it will be apparent that various changes and modifications may be made therein without departing from the spirit and scope of the present invention as defined in the appended claims.

What is claimed is:

1. A sunscreen composition comprising:
   (a) at least one sunscreen agent; and
   (b) at least one glucoside emulsifier selected from the group consisting of cocoyl glucoside, cocoyl glucoside/cetearyl alcohol, cocoyl ethyl glucoside, disodium coco-glucoside citrate, disodium coco-glucoside sulfosuccinate, lauroyl ethyl glucoside, myristoyl ethyl glucoside, octyl dimethicone ethoxy glucoside, oleoyl ethyl glucoside, sodium coco-glucoside tartrate, and any mixtures thereof,
   wherein said at least one glucoside emulsifier imparts an enhanced soft, silky feel to the composition.

2. The composition of claim 1, wherein said at least one sunscreen agent is selected from the group consisting of: para-aminobenzoic acid (PABA), avobenzone, benzophenone-1, benzophenone-2, benzophenone-3, benzophenone-4, benzophenone-6, benzophenone-8, benzophenone-12, methoxycinnamate, ethyl dihydroxypropyl-PABA, glyceryl PABA, homosalate, methyl anthranilate, octocrylene, octyl dimethyl PABA, octyl methoxycinnamate, octyl salicylate, PABA, 2-phenylbenzimidazole-5-sulphonic acid, triethanolamine salicylate, 3-(4-methylbenzylidene)-camphor, red petrolatum, zinc oxide, titanium dioxide, 3-(4-methylbenzyldine)boran-2-one(methylbenzindinecamphor), benzotriazole, phenylbenzimidazole-5-sulfonic acid, methylene bis-benzotrizolyl tetramethylbutyl phenol, and any mixtures thereof.

3. The composition of claim 1, wherein said at least one sunscreen agent is selected from the group consisting of: avobenzone, benzophenone-3, octyl methoxycinnamate, octyl salicylate, zinc oxide, and any mixtures thereof.

4. The composition of claim 1, wherein said at least one sunscreen agent is about 1 wt. % to about 40 wt. % of the total weight of the composition.

5. The composition of claim 1, wherein said at least one glucoside emulsifier is cocoyl glucoside/cetearyl alcohol.

6. The composition of claim 1, wherein said at least one glucoside emulsifier is about 1 wt. % to about 10 wt. % of the total weight of the composition.

7. The composition of claim 1, further comprising one or more additional emulsifiers other than a glucoside emulsifier.

8. The composition of claim 7, wherein said one or more additional emulsifiers are selected from the group consisting of: butylated PVP, cetyl alcohol, sodium acrylate/sodium acryloyldimethyltaurate copolymer, diethylhexyl napthalate, sorbitan oleate, sorbitan sesquioleate, sorbitan isostearate, sorbitan trioleate, polyglyceryl-3-diisostearate, polyglycerol ester of oleic/isostearic acid, polyglyceryl-6 hexaricinolate, polyglyceryl-4-oleate, polygylceryl-4 oleate/PEG-8 propylene glycol cocoate, oleamide DEA, sodium glyceryl oleate phosphate, hydrogenated vegetable glycerides phosphate, and any mixtures thereof.

9. The composition of claim 7, wherein said one or more additional emulsifiers are selected from the group consisting of: butylated PVP, cetyl alcohol, sodium acrylate/sodium acryloyldimethyltaurate copolymer, diethylhexyl napthalate, and any mixtures thereof.

10. The composition of claim 1, further comprising one or more emollients.

11. The composition of claim 10, wherein said one or more emollients is selected from the group consisting of: cyclomethicone, dimethicone, dicapryl maleate, caprylic/capric triglyceride, mineral oil, lanolin oil, coconut oil, cocoa butter, olive oil, aloe extracts, jojoba oil, castor oil, fatty acid, fatty alcohol, diisopropyl adipate, hydroxybenzoate ester, benzoic acid ester of $C_9$–$C_{15}$ alcohols, isononyl iso-nonanoate, alkane, silicone, ether, $C_{12}$–$C_{15}$ alkyl benzoate, and any mixtures thereof.

12. The composition of claim 10, wherein said one or more emollients is selected from the group consisting of: cyclomethicone, dimethicone, dicapryl maleate, caprylic/capric triglyceride, aloe vera, and any mixtures thereof.

13. The composition of claim 10, wherein said emollient is present in an amount about 0.10 wt. % to about 30 wt. % of the total weight of the composition.

14. The composition of claim 1, further comprising water.

15. The composition of claim 14, wherein said water is present in an amount about 45 wt. % to about 75 wt. % of the total weight of the composition.

16. The composition of claim 1, further comprising one or more additional components selected from the group consisting of: skin-feel additive, moisturizing agent, film former/waterproofing agent, pH adjuster/chelating agent, preservative, and any mixtures thereof.

17. The composition of claim 16, wherein said skin-feel additive is selected from the group consisting of: synthetic polymers, silicones, esters, particulates, and any mixtures thereof.

18. The composition of claim 17, wherein said skin-feel additive is nylon-12.

19. The composition of claim 17, wherein said skin-feel additive is present in an amount about 0.10 wt. % to about 5 wt. % of the total weight of the composition.

20. The composition of claim 16, wherein said moisturizing agent is a humectant.

21. The composition of claim 20, wherein said humectant is selected from the group consisting of: glycerin, polyethylene glycol, polypropylene glycol, sorbitol, PEG-4, and any mixtures thereof.

22. The composition of claim 16, wherein said moisturizing agent is present in an amount about 0.10 wt. % to about 1 wt. % of the total weight of the composition.

23. The composition of claim 16, wherein said film former/waterproofing agent is selected from the group consisting of: polyethylene, synthetic wax, and any mixtures thereof.

24. The composition of claim 16, wherein said film former/waterproofing agent is present in an amount about 0.10 wt. % to about 5 wt. % of the total weight of the composition.

25. The composition of claim 16, wherein said pH adjuster/chelating agent is selected from the group consisting of: sodium hydroxide, triethanolamine, trisodium ethylenediaminetetraacetic acid, and any mixtures thereof.

26. The composition of claim 1, wherein the composition has a pH about 3 to about 9.

27. The composition of claim 16, wherein said preservative is selected from the group consisting of: diazolidinyl urea, iodopropynyl butylcarbamate, chloromethylisotiazolinone, methylisothiazolinone, vitamin E and its derivatives, vitamin C, butylated hydroxytoluene, methylparaben, and any mixtures thereof.

28. A sunscreen composition comprising:
(a) about 6 wt. % to about 12 wt. % of one or more sunscreens; and
(b) about 4 wt. % to about 6 wt. % cocoyl glucoside mixed with cetearyl alcohol,
wherein said cocoyl glucoside mixed with cetearyl alcohol imparts a soft, silky feel to the composition when applied to a user's skin.

29. The composition of claim 28, wherein said one or more sunscreens are selected from the group consisting of: octyl methoxycinnamate, octyl salicylate, butyl methoxydibenzoylmethane, and any mixtures thereof.

30. The composition of claim 28, further comprising nylon-12, wherein said nylon-12 further imparts a soft, silky feel to the composition when applied to a user's skin.

31. The composition of claim 28, further comprising one or more additional components selected from the group consisting of: emulsifier other than glucoside, emollient, skin-feel additive other than nylon-12, moisturizing agent, film former/waterproofing agent, pH adjuster/chelating agent, preservative, and any mixtures thereof.

32. The composition of claim 28, wherein the composition has a SPF of at least 15.

33. A sunscreen composition comprising:
(a) about 15 wt. % to about 25 wt. % of one or more sunscreens; and
(b) about 4 wt. % to about 6 wt. % cocoyl glucoside mixed with cetearyl alcohol,
wherein said cocoyl glucoside mixed with cetearyl alcohol imparts a soft, silky feel to the composition when applied to a user's skin.

34. The composition of claim 33, wherein said one or more sunscreens are selected from the group consisting of: octyl methoxycinnamate, octyl salicylate, benzophenone-3, butyl methoxydibenzoylmethane, and any mixtures thereof.

35. The composition of claim 33, further comprising nylon-12, wherein said nylon-12 further imparts a soft, silky feel to the composition when applied to a user's skin.

36. The composition of claim 33, further comprising one or more additional components selected from the group consisting of: emulsifier other than glucoside, emollient, skin-feel additive other than nylon-12, moisturizing agent, film former/waterproofing agent, pH adjuster/chelating agent, preservative, and any mixtures thereof.

37. The composition of claim 33, wherein the composition has a SPF of at least 30.

38. A sunscreen composition comprising:
(a) about 20 wt. % to about 30 wt. % of one or more sunscreens; and
(b) about 4 wt. % to about 6 wt. % cocoyl glucoside mixed with cetearyl alcohol,
wherein said cocoyl glucoside mixed with cetearyl alcohol imparts a soft, silky feel to the composition when applied to a user's skin.

39. The composition of claim 38, wherein said one or more sunscreens are selected from the group consisting of: octyl methoxycinnamate, octyl salicylate, benzophenone-3, zinc oxide mixed with $C_{12\text{-}15}$ alkyl banzoate, and any mixtures thereof.

40. The composition of claim 38, further comprising one or more additional components selected from the group consisting of: emulsifier other than glucoside, emollient, skin-feel additive, moisturizing agent, film former/waterproofing agent, pH adjuster/chelating agent, preservative, and any mixtures thereof.

41. The composition of claim 38, wherein the composition has a SPF of at least 50.

* * * * *